United States Patent [19]
Giragosian et al.

[11] Patent Number: 5,592,078
[45] Date of Patent: Jan. 7, 1997

[54] METHOD AND APPARATUS FOR MOVING ALONG A BOUNDARY BETWEEN ELECTROMAGNETICALLY DIFFERENT MATERIALS

[75] Inventors: David W. Giragosian, Ridgefield; James R. Norris, Jr., Georgetown; Howard A. Sholl, Storrs, all of Conn.

[73] Assignee: Dapco Industries, Inc., Ridgefield, Conn.

[21] Appl. No.: 346,026

[22] Filed: Nov. 29, 1994

[51] Int. Cl.[6] .............................. G01B 7/14; G01N 29/04; G05B 19/33; B23K 9/12
[52] U.S. Cl. ................ 324/207.18; 73/601; 219/124.34; 318/576; 324/233; 324/226; 324/243
[58] Field of Search ..................... 324/67, 207.17, 324/207.18, 207.19, 226, 233, 239–243, 262, 326, 329; 318/576, 587; 73/601; 180/167, 168; 219/124.1, 124.34

[56] References Cited

U.S. PATENT DOCUMENTS

| | | | |
|---|---|---|---|
| 3,017,496 | 1/1962 | Greene | 318/576 X |
| 3,201,562 | 8/1965 | Anderson | 318/576 X |
| 3,359,486 | 12/1967 | Brosious | 324/233 |
| 3,394,303 | 7/1968 | Cressman et al. | 324/243 X |
| 3,430,134 | 2/1969 | Flaherty et al. | 324/243 |
| 4,303,883 | 12/1981 | Mori et al. | 324/243 X |
| 4,823,082 | 4/1989 | Nasu et al. | 324/242 X |

OTHER PUBLICATIONS

Technical Information brochure from Keyence for Welding Position Detector, Dec., 1992, 2 pages.

*Primary Examiner*—Gerard R. Strecker
*Attorney, Agent, or Firm*—Ware, Fressola, Van Der Sluys & Adolphson

[57] ABSTRACT

A detector and tracker using a three coil sensor for is disclosed. The detector detects eddy current variations caused by differences in electromagnetic characteristics in two adjacent materials. The eddy current variations are measured and compared to determine the magnitude and direction the detector may be from the center of one of the adjacent materials. The magnitude and direction determination by the detector can be used to drive a process controller to position the sensor.

3 Claims, 4 Drawing Sheets

MAJOR STAGES—RECEIVING CIRCUITRY

SENSOR COIL ARRANGEMENT

MAJOR STAGES—RECEIVING CIRCUITRY 5,592,078

METHOD AND APPARATUS FOR MOVING ALONG A BOUNDARY BETWEEN ELECTROMAGNETICALLY DIFFERENT MATERIALS

BACKGROUND OF THE INVENTION

1. Field of the Invention

The present invention relates to the detection of electromagnetically differing materials. More particularly, the present invention relates to detection and tracking of welds, wires embedded in composite materials and seams on electric wires through the detection of variations in eddy currents generated in the material being examined.

2. Description of the Prior Art

Generally, the detection of seams in electric wire, wires embedded in composite materials or welds is an integral part of monitoring and managing process or quality control of a manufacturing process. More particularly, the tracking of electric resistance welds (ERWs) is an integral function of process control during the manufacture of ERW tubes. Maintaining alignment of equipment on a weld is a critical requirement, whether it is used to keep the weld centered beneath an annealing head, or to keep weld inspection sensors centered over the weld during the inspection process. Alignment is particularly important when the integrity of the welded area is tested using ultrasonic flaw detection techniques.

One prior art method of tracking welds consists of painting a stripe offset from the weld and then tracking the paint stripe using video cameras. This prior art process has drawbacks in that it is cumbersome, adds process steps and expense to the testing process.

Another prior art method for tracking welds uses a high frequency ultrasonic transducer in an attempt to delineate the weld zone by the backscatter induced by the grain structure of the weld itself. However, this process is limited because it does not produce consistent results.

SUMMARY OF THE INVENTION

The present invention is designed to overcome the limitations that are attendant upon the use of the prior art described above, and toward this end, it contemplates the provision of an apparatus for moving along the boundary between a first material having different electromagnetic properties than an adjacent second material. The apparatus comprises a three coil sensor, a detector circuit, and a process controller. The three coil sensor includes a transmitting coil having an input and two adjacent receiving coils each having an output. The input of the transmitting coil and the outputs of the receiving coils are electrically connected to the detection circuit. The detection circuit provides a driving signal for the transmitting coil, receives and processes signals from the receiving coils to provide a control signal representative of the position of the sensor relative to the center of the weld. The control signal is used by the process controller to drive of stepping motors, to keep an ultrasonic sensor positioned over the weld.

According to the present invention, in the detector circuit, a low frequency signal from a reference oscillator is fed through a buffering amplifier to the input of the transmitting coil so as to drive the transmitting coil with a low frequency sine-wave signal. The signal from the reference oscillator is also fed through a variable gain amplifier stage that is used to form a square-wave reference signal for a phase comparator stage, as further described below. The receiving coils receive a portion of the low frequency transmitted signal from the transmitting coil, the portion depending on the position of each of the receiving coils relative to a weld. Each of the received signals from the receiving coils is fed through a bandpass filter to a cross-coupled dual amplifier circuit that provides an initial gain stage for each received signal. The cross-coupled amplified signals are fed to a phase shift amplifier stage. In the phase shift amplifier stage, the phase and gain of one of the received signals may be adjusted with respect to the phase and gain of the other. The phase shifted signals are combined by a differential amplifier to form a single bipolar signal capable of indicating the direction and magnitude (distance) that the sensor is from the center of the weld based on the dominating signal's phase. The resulting bipolar signal from the combining amplifier stage is passed through a bandpass filter and a final amplifying stage. The signal from the amplifying stage as well as the square-wave reference signal described above are each fed to a phase comparator stage. The phase comparator stage compares the phase of the signal from the final amplifying stage with the phase of the square wave reference signal and generates a DC signal at its output proportional to that comparison. The DC signal may be used as an input for a device that can annunciate the signal (e.g. an oscilloscope) or can be used as an input to a process controller, programmable logic controller, or other device that can provide control of position.

According to the present invention, when the weld detector is balanced, that is, when the sensor is centered over the weld so that the receiving coils of the sensor are equidistant from the weld, the gain and phase of one of the cross-coupled amplifier's output signals may be calibrated so as to produce a zero output voltage at the output of the phase comparator. When the sensor is positioned left or right of the center position, the signal from the receiving coil closest to the weld will dominate. Because the two received signals from the receiving coil are opposite in polarity, a bipolar DC voltage is derived that indicates the magnitude and direction the sensor is "off center" from the weld.

BRIEF DESCRIPTION OF THE DRAWINGS

The drawings, not drawn to scale, include.

DETAILED DESCRIPTION OF THE PRESENT INVENTION

Figure 1:
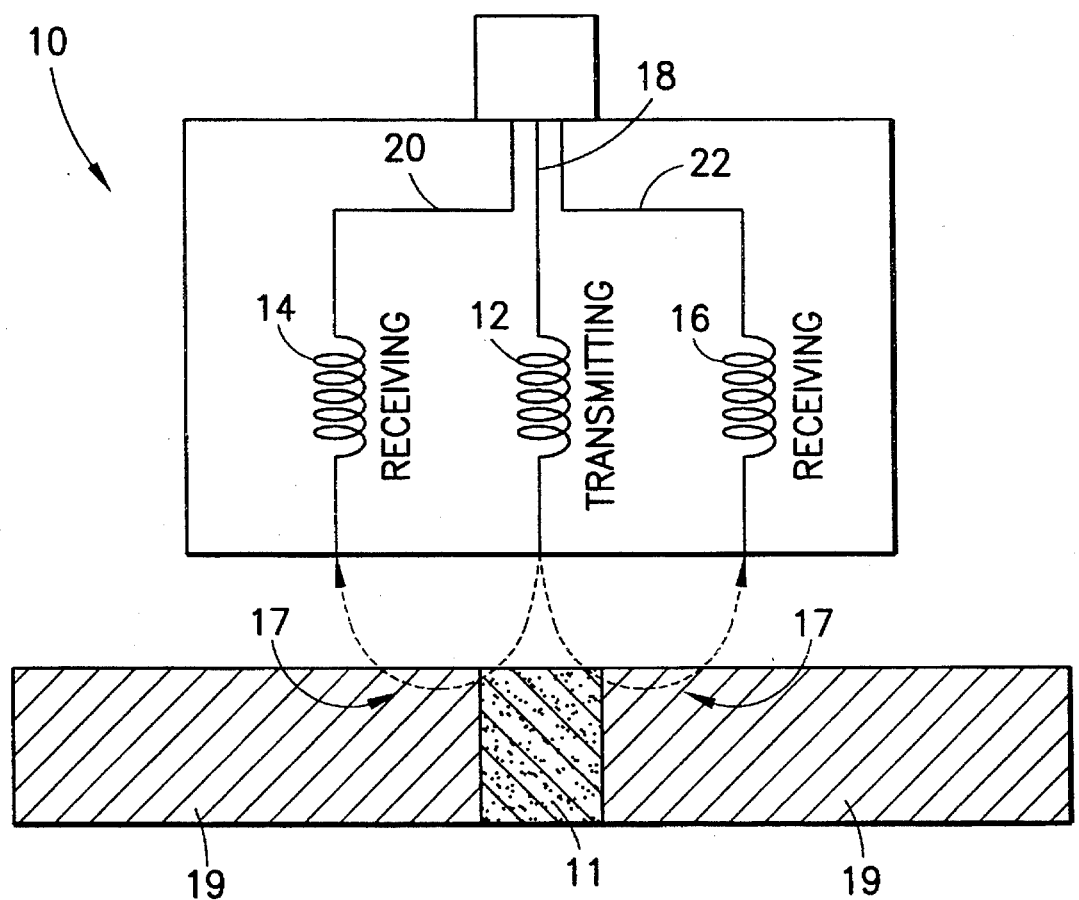
FIG. 1, which is a schematic diagram of an embodiment of a sensor coil assembly positioned over a weld joining two members together, the members and the weld shown in cross-section.

Referring to FIG. 1, there is illustrated a sensor 10 for sensing a weld 11. The sensor 10 houses three coils, a transmitting coil 12, and two receiving coils 14 and 16 located equally adjacent to, but on opposite sides of the transmitting coil 12. The transmitting coil 12 has an input 18 and the two receiving coils have outputs 20 and 22 respectively connected to a detection circuit 30, shown in FIG. 2.

When the sensor 10 is positioned over the weld 11 so that the transmitting coil 12 is positioned directly over the weld 11, each of the receiving coils 14 and 16 forms a magnetic circuit with the transmitting coil 12, the weld 11 and the material 17 in proximity thereto forming part of members 19. The magnetic circuit formed by the coil arrangement generates eddy currents in the weld 11 and adjacent material 17 as a result of exciting transmitter coil 12 with a low frequency AC signal, such as a 3 KHz sine wave signal. The eddy currents in the material create additive loss (e.g. higher resistivity) and thus affect the coils' impedance. As will be described more fully below, the coils' impedance is measured with the detection circuit 30 shown in FIG. 2. To the extent that a weld 11 is electromagnetically different from the adjacent material 17, the detection circuit 30 can detect the difference. If a weld 11 was perfect, in the sense that it having no difference in electromagnetic properties as compared to the adjacent material 17, the detector 30 would be unable to detect a difference.

Figure 2:
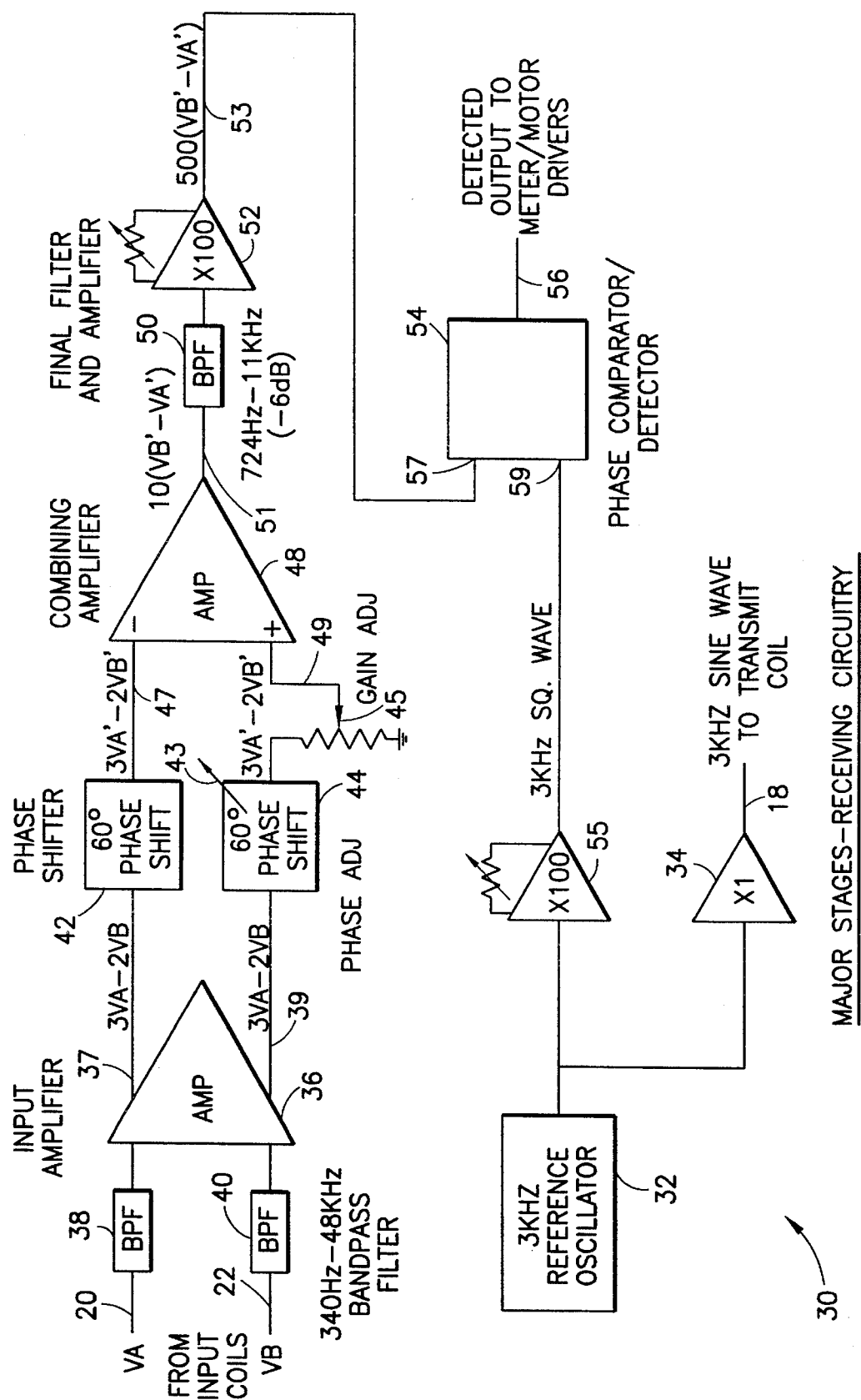
FIG. 2, which is a block diagram of one embodiment of a detector circuit of the present invention.

Referring to FIG. 2, there is illustrated the detection circuit 30 of the present invention. According to the present invention, a reference oscillator 32 is used to generate a low frequency (3 Khz) signal to drive the input 18 of the transmitting coil 12 via a buffering amplifier 34 which provides ±200 ma of drive current for the coil 12. Depending on the positioning of the sensor, each of the receiving coils 16 and 18 receives a portion of the transmitted signal from the transmitting coil 12.

Received signals VA and VB of the receiving coils 14 and 16 are fed to a cross-coupled dual amplifier circuit 36 via two bandpass filters 38 and 40 having a lower cutoff frequency of 340 Hz and an upper cutoff frequency of 48 Khz. Both signals VA and VB have a center frequency of approximately 3 KHz, which is near the midpoint of bandpass filters 38 and 40. Also, there are input resistors (not shown) to provide a resistive load for each of the receiving coils 14 and 16. The cross-coupled dual amplifier circuit 36 provides an initial gain stage as well as crossing the signals VA and VB so as to obtain some common signal rejection at its outputs 37 and 39.

By interconnecting and floating the virtual ground connections of the two amplifier stages of the cross-coupled dual amplifier circuit 36, both received signals VA and VB are mixed to form output signals at outputs 37 and 39 of magnitude (3VA–2VB) and (3VB–2VA), respectively. (For the sake of simplicity, intermediate signals throughout the detection circuit 30 will be referred to hereinafter by their signal components and magnitudes). As explained above, this mixing of input signals VA and VB in the dual amplifier circuit 36 provides some common signal rejection.

Signals (3VA–2VB) and (3VB–2VA) are fed to standard phase shift amplifier stages 42 and 44 comprising a delay network (not shown) and a differential amplifier (not shown). The phase shift amplifier stage 44, further includes circuitry for adjusting the phase and gain of signal (3VB–2VA) with respect to the phase and gain of signal (3VA–2VB) by means of potentiometers 43 and 45. In the phase shift amplifier stages, the phase of signals (3VA–2VB) and (3VB–2VA) are shifted approximately 60 degrees in opposite directions from their respective original phases and a gain of approximately unity is applied thereto to obtain phase shifted and amplified signals (3VA'–2VB') and (3VB'–2VA') ("'" indicating a 60 degree phase shift from the original phase) on lines 47 and 49, respectively. The phase shift amplifier stage 44 with potentiometers 41 and 43 for phase and gain adjustment allows calibration of the sensor 10 and detection circuit 30 by careful matching both the phase and gain of each signal (3VA–2VB) and (3VB–2VA) so that signal cancellation can occur in a later stage of the detection circuit 30 when the transmitting coil 12 of the sensor 10 is directly over the center of the weld 11. Because the phase adjustment affects the gain, but the gain adjustment does not affect the phase, those skilled in the art will appreciate that phase adjustment should be made first, followed by adjustment in the gain. The adjustment of phase and gain may be made by monitoring signals (3VA'–2VB') and (3VB'–2VA') at lines 47 and 49 on an oscilloscope, LEDs or an analog/digital voltmeter. Also, adjustments may be made by monitoring the detection circuit's 30 output signal 56 after the received signals have been combined in later stages.

Phase shifted and amplified signals (3VA'–2VB') and (3VB'–2VA') are combined and amplified in a differential combining amplifier stage 48. In the preferred embodiment, the combining amplifier stage 48 has a gain of two. Subtraction of signal (3VA'–2VB') from signal (3VB'–2VA') in the combining amplifier stage and the application of a gain of two results in a single output signal having a magnitude of 10(VB'–VA') at output 51.

Further filtering and amplification of signal 10(VB'–VA') is accomplished by passing the signal through a bandpass filter 50 having a 6 dB loss and a variable gain amplifier circuit 52 having a 40 dB gain. This filtering and amplification results in a signal having a magnitude 500(VB'–VA') at output 53. In the preferred embodiment, bandpass filter 50 has a lower cutoff frequency of 724 Hz and an upper cutoff frequency of 11 Khz. The variable gain amplifier 52 permits adjustment of the gain of signal 500(VB'–VA') so as to allow the detection circuit 30 to be calibrated for different sensors 10 that may have differing sensitivities due to the properties of particular transmit and receive coil assemblies.

Amplifier output 53 is connected to an input 57 of a phase comparator 54 comprising a balanced modulator/demodulator IC configured as a phase detection circuit, to provide the input 57 with signal 500(VB'–VA'). A 3 Khz reference signal from the reference oscillator 32 is fed to another input 59 of the phase comparator 54 through a 40 dB gain variable amplifier 55. The variable gain amplifier 55 forms a square-wave reference signal for the comparator 54. In the comparator 54, the phase of signal 500(VB'–VA') at input 57 is compared with the phase of the reference signal at input 59. The phase comparator 54 acts as a position detector, based on the above described comparison of phases, so as to generate a DC signal at output 56 proportional to the direction and distance that the sensor 10 is positioned with respect to the center of the weld 11. When the sensor 10 is centered over the weld 11, and signals VA and VB are calibrated through the previously described phase and gain adjustments to produce a zero output voltage. The detection circuit 30 is then considered balanced. When the sensor is moved off center from the weld 11, then either received signal VA or VB dominates in the detection circuit and a DC signal is generated that has a positive or negative value as well as a magnitude that depends upon the position of the transmitting coil 12 relative to the weld 11. As the sensor moves away from the weld, the magnitude of the DC signal increases. Since signals VA and VB are opposite in polarity, a bipolar DC signal is derived. This DC signal can be used for control functions or simple monitoring.

Figure 3:
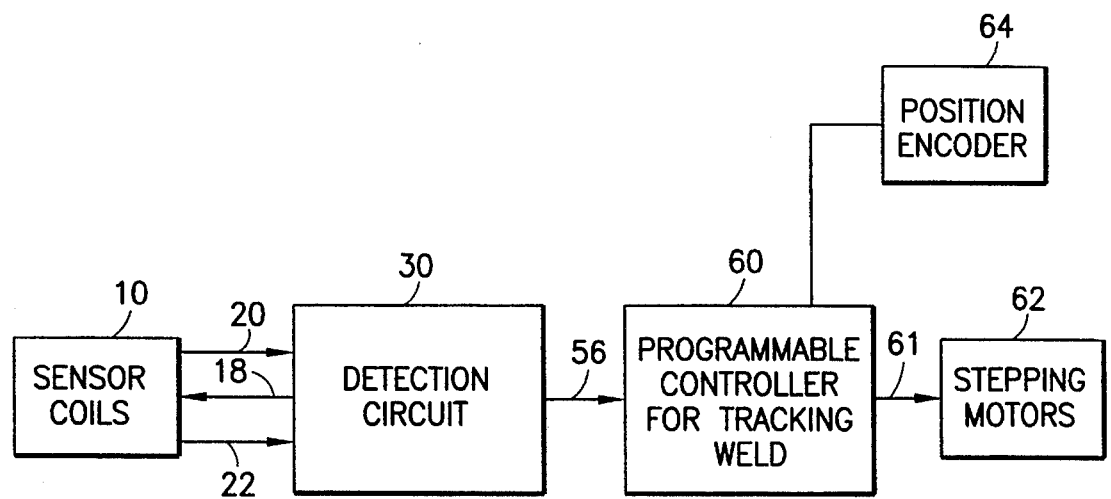
FIG. 3, which is a block diagram of a weld tracker.

Referring to FIG. 3, those skilled in the art will appreciate that position control may be accomplished using the weld detector of the present invention through connection of output 56 to a programmable logic controller 60 which is used to drive stepping motors 62 through line 61. Based on the polarity and magnitude of the output signal 56, the programmable controller 60 may drive the stepping motors 62 accordingly to reposition the sensor 10 over the center of the weld should it deviate therefrom or position the sensor 10 relative to the weld 11. A position encoder 64 may also be attached to the programmable controller 60 to aid the controller 60 in the event that tracking is lost or interrupted, as described more fully below, or to enable logging of weld tracking information.

Figure 4:
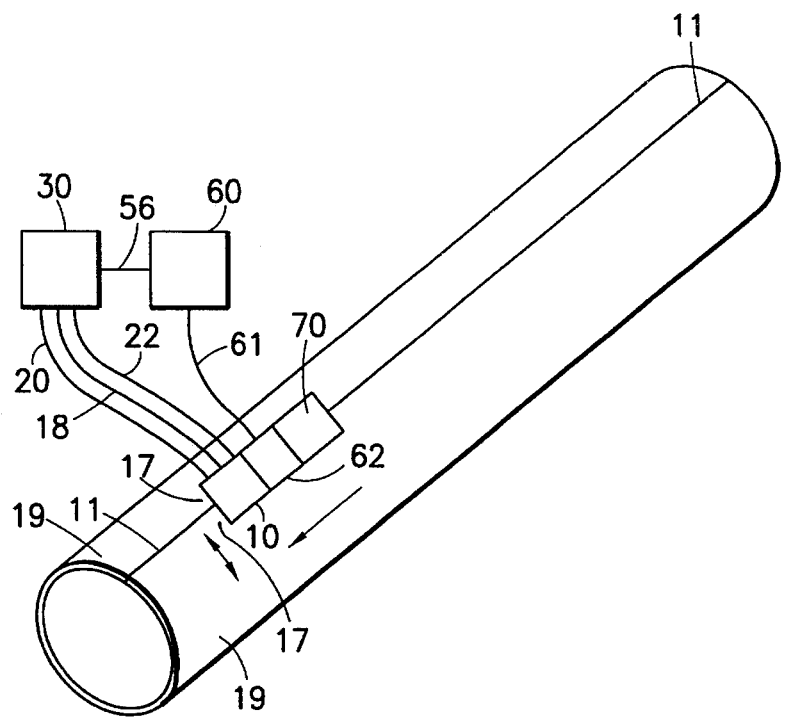
FIG. 4, which is a schematic diagram of a weld being examined using the weld detector circuit as part of a weld tracker of the present invention to guide the examination.

FIG. 4 schematically illustrates a welded pipe undergoing ultrasonic inspection with an apparatus for inspecting welds comprising the sensor 10, detector circuit 30, programmable controller 60, stepping motors 62, previously described, and an ultrasonic weld inspection sensor 70. The ultrasonic weld inspection sensor 70 is kept in a position substantially centered over the weld 11 by the present invention as it is moved along the weld. Also, those skilled in the art will appreciate that the ultrasonic weld inspection sensor 70 may be also be positioned offset from the center of the weld 11, if desired.

Figure 5:
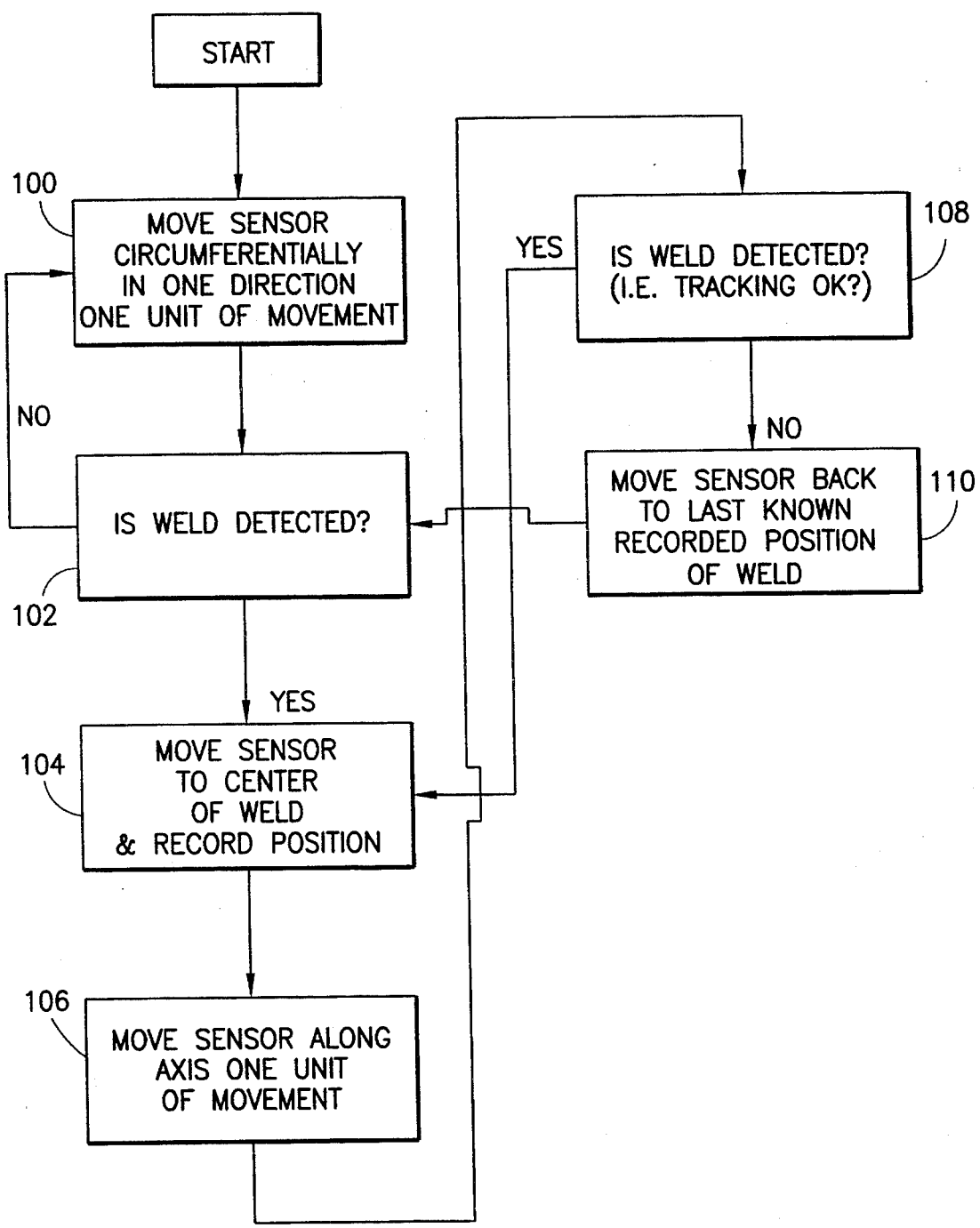
FIG. 5, which is a flow diagram of a method for tracking a weld.

Referring to FIG. 5, the sensor 10, detection circuit 30, programmable controller 60, and stepping motors 62, may be used as part of a method to automatically first locate the center of the weld 11 prior to performing tracking thereof by moving the sensor 10 along the surface of the pipe 19 until the weld 11 is detected. Once the weld 11 is detected tracking may be commenced. If tracking is interrupted or lost, sensor 10, detection circuit 30, programmable controller 60, stepping motors 62, and position encoder 64 may be employed in a method to reacquire tracking of the weld 11 when tracking is lost by returning the sensor 10 to a previously known position on the weld 11 and resuming tracking therefrom. More particularly according to FIG. 5, the method is initated at step 100 where the sensor 10 is moved circumferentially about the pipe one unit of movement. A determination is made as to whether the weld is detected in step 102. Step 100 is repeated until the weld is detected in step 102. Once the weld is detected, the sensor 10 is centered over the weld in step 104 and the position of the sensor 10 based on position encoder 62 is recorded by the controller 60. The sensor 10 is then moved axially one unit of movement in step 106. After the sensor 10 is moved according to step 106, a determination is made as to whether a weld is detected in step 108. If a weld is detected, step 104 is followed. If no weld is detected in step 108 then, as shown in step 110, the sensor 10 is moved back to last recorded position that the weld was detected and the detection cycle is restarted at step 102.

While the example of the application of invention described above involves the detection and tracking of welds, it should be appreciated that the invention is not limited thereto. In fact, the invention may be used to detect and track eddy current variations in any material. For example, the invention could be used to track a wire embedded in a composite material as long as the wire and the composite material have detectably different electromagnetic properties.

Thus, what has been described is an apparatus useful for detecting and tracking electromagnetically diferring materials, such as welds. The embodiments of the apparatus disclosed herein admirably achieve the objects of the present invention; however, it should be appreciated by those skilled in the art that departures can be made by those skilled in the art without departing from the spirit and scope of the invention which is limited only by the following claims.

What is claimed is:

1. An apparatus for moving along a boundary between a first material having different electromagnetic properties than an adjacent second material, the apparatus comprising:

a sensor, the sensor further comprising a transmitting coil, and first and second receiving coils positioned adjacent to the transmitting coil;

a detection circuit, the detection circuit further comprising:
  a driving subcircuit for driving the transmitting coil with a low frequency input signal;
  a signal processing subcircuit for receiving signals from the first and second receiving coils and for processing and combining the signals received by the first and second receiving coils so as to generate a single bipolar signal whose phase polarity is proportional to the position of the sensor relative to the boundary between the first material and the second material being detected;
  a comparison subcircuit for comparing the single bipolar signal to a reference signal representative of the input signal to the transmitting coil and for generating a control signal in proportion to a result of the comparison of the reference signal to the single bipolar signal;

a position encoder for providing a signal representing the position of the apparatus; and a process controller responsive to the control signal for moving the apparatus along the boundary between the first material and the second material, the process controller further comprising means, responsive to the position encoder, for moving the apparatus to a known position where the boundary was detected when the apparatus does not detect the boundary.

2. An apparatus for moving along a boundary between a first material having different electromagnetic properties than an adjacent second material, the apparatus comprising:

a sensor, the sensor further comprising a transmitting coil, and first and second receiving coils positioned adjacent to the transmitting coil;

a detection circuit, the detection circuit further comprising:
  a driving subcircuit for driving the transmitting coil with a low frequency input signal, the driving subcircuit further comprising a reference oscillator having an output connected to the transmitting coil through a buffering amplifier, wherein the output signal of the buffering amplifier provides the low frequency input signal to the transmitting coil;
  a signal processing subcircuit for receiving, processing and combining signals from the first and second receiving coils to generate a single bipolar signal whose phase polarity is proportional to the position of the sensor relative to the first material being detected, the signal processing subcircuit further comprising:
    a cross-coupled amplifier for receiving signals from the receiving coils and for providing common signal rejection and amplification of the signals received from the receiving coils, the cross-coupled amplifier having a pair of inputs and a pair of outputs, wherein one of the inputs is connected to one of the receiving coils through a bandpass filter and wherein the other input is connected to the other receiving coil through a bandpass filter;

a pair of phase shifting amplifiers for shifting the phase of the signals received from the receiving coils, wherein one of the phase shifting amplifiers is connected to one of the outputs of the cross-coupled amplifier, wherein the other phase shifting amplifier is connected to the other output of the cross-coupled amplifier, and wherein one of the phase shifting amplifiers has means for adjusting phase and gain;

a combining amplifier for combining signals received from the phase shifting amplifiers to form the single bipolar signal, the combining amplifier having a pair of inputs and a single output, wherein one of the inputs is connected to one of the phase shifting amplifiers and wherein the other input is connected to the other phase shifting amplifier;

a final amplifier for amplifying the single bipolar signal created by the combining amplifier, the final amplifier having an input connected to the output of the combining amplifier through a bandpass filter and an output connected to the comparison subcircuit;

a comparison subcircuit for comparing the single bipolar signal to a reference signal and for generating a control signal in proportion to a result of the comparison of the reference signal to the single bipolar signal, the comparison subcircuit further comprising a reference oscillator for providing the reference signal, a phase comparator for providing the control signal, the phase comparator having a pair of inputs and a single output, wherein one of the inputs is connected to the signal processing subcircuit so as to receive the single bipolar signal created thereby, and wherein the other input is connected to the reference oscillator through an amplifier to receive the reference signal;

a process controller responsive to the control signal for moving the apparatus along the boundary between the first material and the second material, the process controller further comprising means for moving the apparatus to a known position where the boundary was detected when the apparatus does not detect the boundary.

3. A method for moving an apparatus along a boundary between a first material having different electromagnetic properties than an adjacent second material, the method comprising the steps of:

(a) exciting a transmitting coil in a sensor of the apparatus when the sensor is positioned adjacent to the first and second material with a low frequency sine wave excitation signal so as to cause the transmitting coil to transmit a low frequency transmitted sine wave signal through the first and second material;

(b) receiving the low frequency transmitted sine wave signal with a first and second receiving coil adjacent to the transmitting coil in the sensor so as to generate first and second received low frequency sine wave signals, respectively;

(c) shifting the phase of first and second received low frequency sine wave signals relative from their original phase so as to generate phase shifted first and second received low frequency sine wave signals;

(d) combining phase shifted first and second received low frequency sine wave signals to generate a phase shifted single bipolar low frequency sine wave signal;

(e) comparing the phase of the single bipolar low frequency sine wave signal to a reference low frequency square wave signal having a frequency and phase substantially the same as the low frequency sine wave excitation signal used to excite the transmitting coil in step (a);

(f) generating a bipolar direct current (DC) signal having a polarity and magnitude, wherein the polarity and magnitude of said signal is proportional to the direction and distance between the transmitting coil and the boundary based upon the comparison in step (e);

(g) moving the apparatus to a new position relative to the first material based on the polarity and magnitude of the bipolar DC signal;

(h) storing the location of the new position of the apparatus;

(i) moving the apparatus to an arbitrary second new position;

(j) repeating steps (a) through (f);

(k) determining whether the sensor detects the presence of the first material;

(l) moving the apparatus from the arbitrary second new position back to the stored new position when it is determined in step (k) that the sensor does not detect the presence of the first material; and (m) moving the apparatus from the arbitrary second new position to a third new position relative to the first material based on the bipolar DC signal when it is determined in step (k) that the sensor detects the presence of the first material; and (n) repeating steps (h) through (m).

* * * * *